United States Patent
Mertens et al.

(10) Patent No.: US 7,332,689 B2
(45) Date of Patent: Feb. 19, 2008

(54) TACKING METHOD AND APPARATUS

(75) Inventors: Steven P. Mertens, New Hope, MN (US); Afsar Ali, Maple Grove, MN (US); Thomas J. Holman, Minneapolis, MN (US); Leo M. Klisch, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 666 days.

(21) Appl. No.: 10/449,454

(22) Filed: May 30, 2003

(65) Prior Publication Data

US 2004/0004311 A1 Jan. 8, 2004

Related U.S. Application Data

(63) Continuation-in-part of application No. 10/082,869, filed on Feb. 26, 2002, now abandoned.

(51) Int. Cl.
*B23K 26/20* (2006.01)

(52) U.S. Cl. .............. 219/121.63; 219/121.82; 219/160; 219/161; 623/921

(58) Field of Classification Search .............. 219/121.63–121.72, 121.82, 160, 161; 623/921
See application file for complete search history.

(56) References Cited

U.S. PATENT DOCUMENTS

| | | | | |
|---|---|---|---|---|
| 3,394,705 A | | 7/1968 | Abramson | 128/349 |
| 3,599,961 A | * | 8/1971 | Morgan | 269/185 |
| 3,867,017 A | * | 2/1975 | Bliss et al. | 359/740 |
| 4,037,599 A | | 7/1977 | Raulerson | 128/214.4 |
| 4,072,146 A | | 2/1978 | Howes | 128/2.05 D |
| 4,493,696 A | | 1/1985 | Uldall | 604/43 |
| 4,574,173 A | | 3/1986 | Bennett | 219/10.53 |
| 4,742,981 A | * | 5/1988 | Converse | 248/231.71 |
| 4,872,189 A | * | 10/1989 | Frankel et al. | 378/119 |
| 4,979,180 A | * | 12/1990 | Muncheryan | 372/92 |
| 5,053,004 A | | 10/1991 | Markel et al. | 604/43 |
| 5,167,623 A | | 12/1992 | Cianci et al. | 604/43 |
| 5,207,648 A | | 5/1993 | Gross | 604/164 |

(Continued)

FOREIGN PATENT DOCUMENTS

JP 402200388 A * 8/1990

(Continued)

*Primary Examiner*—Samuel M. Heinrich
(74) *Attorney, Agent, or Firm*—Vidas, Arrett & Steinkraus, P.A.

(57) ABSTRACT

An apparatus for tacking a multi-lumen tubular assembly together comprises a laser, an optical member and a placement tray for retaining the tubular assembly. A portion of the optical member defines a window that is substantially transparent to laser energy emitted from the laser. The window has a substantially concave shaped surface. The placement tray and the window surface define a processing area for positioning at least a portion of the tubular assembly. The processing area receives the laser energy that is emitted from the laser and passed through the window of the optical member. The tubular assembly is defined by an outer tubular member disposed about at least a portion of at least one inner tubular member. The laser energy transmitted into the processing area is transmitted substantially through the outer tubular member and is substantially absorbed by at least one region of the least one inner tubular member.

29 Claims, 6 Drawing Sheets

U.S. PATENT DOCUMENTS

| | | | |
|---|---|---|---|
| 5,221,255 A | 6/1993 | Mahurkar et al. | 604/43 |
| 5,221,256 A | 6/1993 | Mahurkar | 604/43 |
| 5,221,515 A * | 6/1993 | Thiebaut et al. | 376/261 |
| 5,315,675 A * | 5/1994 | Dennis et al. | 385/32 |
| 5,421,566 A * | 6/1995 | Morgan | 269/221 |
| 5,540,712 A * | 7/1996 | Kleshinski et al. | 623/1.19 |
| 5,563,391 A * | 10/1996 | Dahm | 219/121.64 |
| 5,585,019 A * | 12/1996 | Gu et al. | 219/121.73 |
| 5,689,864 A * | 11/1997 | White | 24/514 |
| 5,718,678 A | 2/1998 | Fleming, III | 604/43 |
| 5,827,378 A * | 10/1998 | Belenkiy | 148/561 |
| 5,879,499 A | 3/1999 | Corvi | 156/175 |
| 5,906,759 A * | 5/1999 | Richter | 219/121.63 |
| 5,932,170 A * | 8/1999 | Belenkiy | 266/130 |
| 6,077,384 A * | 6/2000 | Collins et al. | 156/345.29 |
| 6,215,099 B1 * | 4/2001 | Livshits | 219/121.76 |
| 6,459,193 B1 * | 10/2002 | Fukuzawa et al. | 313/402 |
| 6,486,437 B2 * | 11/2002 | Tanabe | 219/121.86 |
| 6,528,397 B1 * | 3/2003 | Taketomi et al. | 438/487 |
| 6,673,107 B1 * | 1/2004 | Brandt et al. | 623/1.35 |
| 6,676,892 B2 * | 1/2004 | Das et al. | 419/7 |
| 7,025,865 B2 * | 4/2006 | Ogawa | 205/70 |
| 2004/0070084 A1 * | 4/2004 | Kuramoto et al. | 257/779 |

FOREIGN PATENT DOCUMENTS

| | | | |
|---|---|---|---|
| JP | 404113383 A | * | 4/1992 |
| JP | 07266073 A | * | 10/1995 |
| JP | 08192282 A | * | 7/1996 |
| JP | 410328310 A | * | 12/1998 |
| JP | 02001111155 A | * | 4/2001 |

* cited by examiner

TACKING METHOD AND APPARATUS

CROSS-REFERENCE TO RELATED APPLICATIONS

This application is a Continuation-in-Part of application Ser. No. 10/082,869, filed Feb. 26, 2002 now abandoned, the contents of which is incorporated herein in its entirety by reference.

STATEMENT REGARDING FEDERALLY SPONSORED RESEARCH

Not Applicable

BACKGROUND OF THE INVENTION

Catheters having multiple lumens are well known. Multi-lumen catheters are known to have use in infusion, perfusion, hemodialysis and other procedures. Duallumen catheters used for hemodialysis, for example, provide one lumen for arterial (intake) flow of blood to be purified and one lumen for venous (return) flow of purified blood.

In most cases a multi-lumen catheters may be used as or in the same procedure as other catheter types. For example, a multi-lumen catheter may be suitable for use in PTCA procedures. In typical PTCA procedures, a guiding catheter is percutaneously introduced into the cardiovascular system of a patient through a vessel and advanced through therein until the distal end thereof is at a desired location in the vasculature. A guidewire and a dilatation catheter having a balloon on the distal end thereof are introduced through the guiding catheter with the guidewire sliding through the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with a liquid or gas at relatively high pressures, to radially compress the arthrosclerotic plaque of the lesion against the inside of the artery wall and thereby dilate the lumen of the artery. The balloon is then deflated to a small profile so that the dilatation catheter may be withdrawn from the patient's vasculature and blood flow resumed through the dilated artery.

In the above example the balloon catheter may include a guide wire lumen and an inflation lumen, and may also include one or more additional lumens. In another example a multi-lumen catheter may be suitable for the deliver of implantable medical devices such as stents, grafts, stent-grafts and vena cava filters.

The various types of dual-lumen catheters may include a variety of cross-sectional configurations such as for example: two semi-circular lumens arranged in a side-by-side configuration and formed within a unitary tube which is internally divided by a planar septum; two circular lumens arranged in a side-by-side configuration and formed within a unitary tube separated by a septum; circular and crescent-shaped lumens (or circle-C) arranged in a side-by-side configuration and formed within a unitary tube which is divided internally by a curved septum or wall by attaching the exterior surface of an inner tube along its length to the interior surface of an outer tube; elliptically-shaped and circular lumens arranged in a side-by-side configuration and formed within a unitary tube divided by a curved septum; and circular and annular lumens arranged in a coaxial configuration wherein an inner tube is placed within an outer tube and the lumens are divided by the exterior surface of the inner tube.

Some examples of coaxial, dual-lumen catheters may be found in U.S. Pat. Nos. 4,493,696; 4,037,599 and 5,053,004. Some examples of catheters having a triple-lumen configuration are shown in U.S. Pat. Nos. 4,072,146; 5,221,255; 5,221,256; 5,167,623; 5,207,648; 5,718,876 and 5,879,499.

In many of the known multi-lumen catheter configurations, the lumens are formed by tubular members that extend from the proximal to the distal end of the catheter, or partially therebetween. In some cases the tubular members are engaged together. Where the tubular members are engaged, typically the engagement is at one or both ends of the tubular members and/or includes bonds at specific locations along the length of the catheter.

Known multi-lumen catheter assemblies may be formed according to a variety of different methods. For example tubular members of a catheter may be engaged together at desired location by methods such as by heat welding, chemical welding or bonding, adhesive welding, mechanical engagement, etc. However, known methods of engagement, such as conventional heat welding may inadvertently damage one or more of the tubular members as heat may be transmitted to areas of the tubular members that are adjacent to the intended engagement site. Where heat is applied directly to the outer tubular member, the heat may damage the outer surface of the outer member and/or detrimentally affect its structural and/or performance characteristics.

In addition to the above, many engagement methods and direct tube formation methods, such as extrusion of a multi-tubular assembly, may lead to a formation of excess material, referred to as "webbing", within one or more of the lumens of the assembly. This presence of webbing or other undesired formations may contribute to a condition known as "back boning". The clinical effect of back boning is that when an elongate shaft is torqued, the tubular member fails to display a one to one torque response and has the effect of building input which is then subsequently and suddenly released. Back boning is a phenomenon which may occur in an unbalanced tube and which may be exacerbated by the presence of webbing or other undesired formations.

Accordingly, there is a need in the art for a method of producing a multi-lumen tubular member, such as a catheter, that reduces the potential for damaging the components of the catheter when they are engaged together. Such a method preferably causes one or more regions of the tubular members to be engaged with a minimum of engaged area and which has the ability to affect engagement without leading to imbalance of the resulting catheter assembly.

All U.S. patents and applications and all other published documents mentioned anywhere in this application are incorporated herein by reference in their entirety.

The invention in various embodiments is summarized below. Additional details of the invention and/or additional embodiments of the invention may be found in the Detailed Description of the Invention below.

The abstract provided herewith is intended to comply with 37 CFR 1.72 and is not intended be used in determining the scope of the claimed invention.

BRIEF SUMMARY OF THE INVENTION

The present invention is directed to several embodiments. In at least one embodiment, the invention is directed methods for forming and preparing multi-lumen tubular members. In at least one embodiment, the invention is directed to a method of tacking or otherwise engaging two or more tubular members to one another. In at least one embodiment, the tubular members define one or more lumens of a catheter assembly.

In at least one embodiment, the tubular members may be engaged together along a shared longitudinal surface where one tubular member contacts another tubular member. The engagement between members may be along a tack line which extends continuously or intermittently over the shared length of the tubular members or a portion or portions thereof.

In some embodiments, the invention is directed to a method and/or apparatus for selectively transmitting energy to one or more portions of a multi-lumen assembly. In at least one embodiment the energy is laser energy. In at least one embodiment, the outer tubular member of the assembly is substantially clear to the wavelength of the laser energy. In at least one embodiment, an inner tubular member is constructed of a material that substantially absorbs the laser energy to heat the material. The heat is conductively transmitted to the inner surface of the outer tubular member to weld the outer tubular member and the inner tubular member together.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWINGS

A detailed description of the invention is hereafter described with specific reference being made to the following drawings.

DETAILED DESCRIPTION OF THE INVENTION

Figure 1:
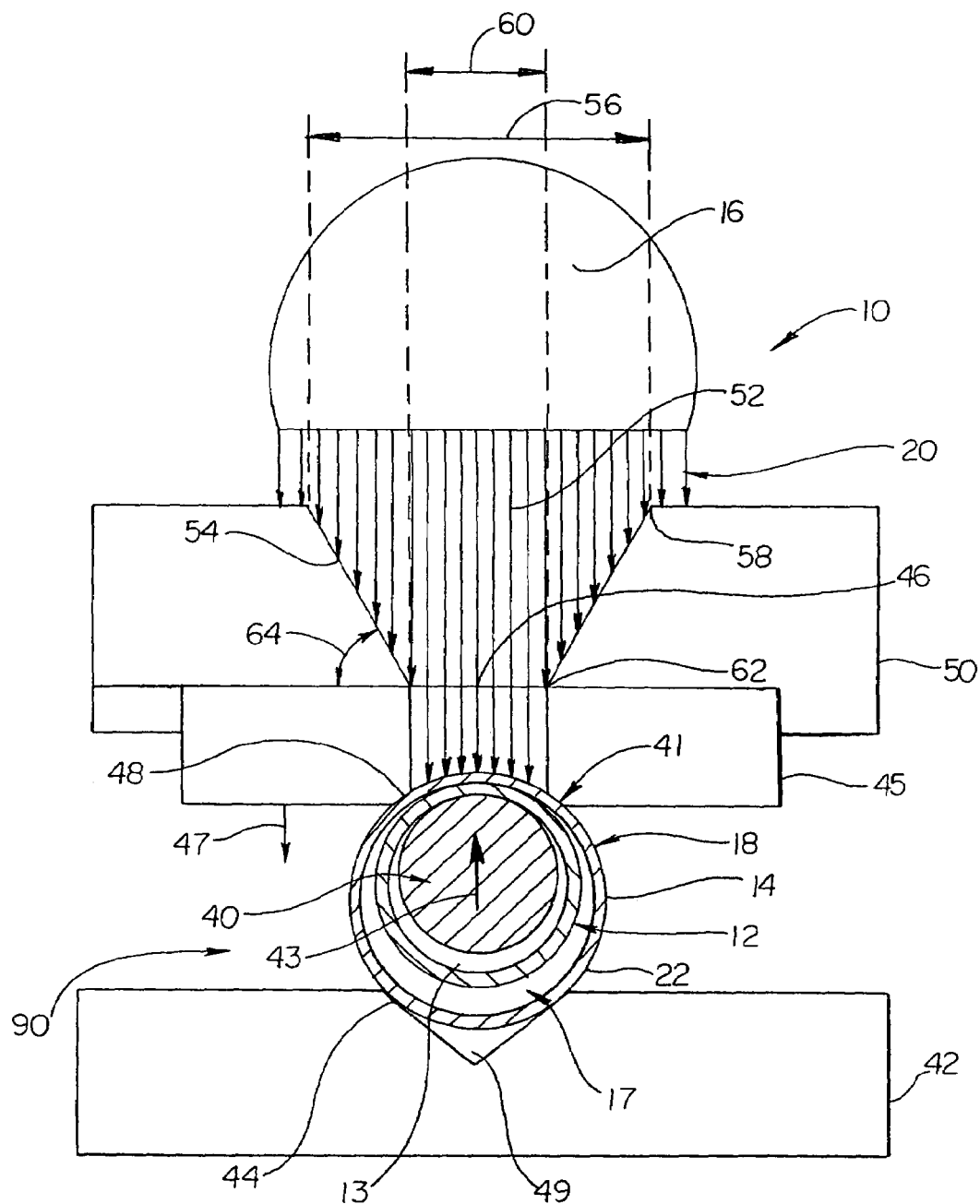
FIG. 1 is a cross-sectional view of an embodiment of the invention.

While this invention may be embodied in many different forms, there are described in detail herein specific preferred embodiments of the invention. This description is an exemplification of the principles of the invention and is not intended to limit the invention to the particular embodiments illustrated.

As indicated above, the present invention is embodied in a variety of forma. For example, in at least one embodiment the invention is directed to a tacking apparatus, shown generally at 10 in FIG. 1, for welding or tacking multiple tubular members of a catheter assembly 18 together. In the embodiment shown in FIG. 1 an inner tubular member 12 and an outer tubular member 14 are shown, however it must be noted that any number of tubular members may be tacked together using the apparatus 10 in accordance with the methods described herein.

In some embodiments members 12 and 14 may be portions of a catheter or catheter assembly such as a proximal inner tube or shaft and a distal outer tube or shaft respectively.

Outer tubular member 14 defines a lumen 17 within which at least a portion of inner tubular member 12 is positioned. Inner tubular member 12 defines an inner lumen 13.

Apparatus 10 utilizes energy such as laser energy, indicated generally at 20, to selectively weld or tack tubular members 12 and 14 tacked together at one or more locations. Typically, tubular members 12 and 14 may be constructed of a polymeric substance such as for example: polyethylene urethanes, natural rubbers, nylons, segmented polyamide-polyether-polyesters sold under the name Pebax® (Pebax), polyesters (Arnitel), latex, polyether amide, polyolefin copolymer (POC) or Surlyn™, etc. In some embodiments, one or more of the tubular members 12 and 14 are at least partially constructed from one or more metals.

In some embodiments, one or more of the tubular members 12 and 14 are at least partially radiopaque.

In some embodiments, at least a portion of one or more of the tubular members 12 and 14 is a balloon or other expandable device.

Energy 20 is transmitted to the tubular members from one or more energy transmission devices such as a laser or lasers 16. In at least one embodiment laser 16 is a diode laser, however in some alternative embodiments laser 16 may be an IR laser, UV laser, $CO_2$, visible light, or any other form of laser device or combinations thereof.

A goal of the present invention is to effectuate engagement of the tubular members 12 and 14 while minimizing or preventing entirely damage to the outer surface 22 of the outer tubular member 14. In order to accomplish this goal, at least one embodiment of the invention employs an outer tubular member 14 that is constructed of material which is substantially transparent to the laser energy 20, where as the inner tubular member 12 is constructed of material which substantially absorbs the laser energy 20. Alternatively, the laser 16 is selected to provide a wavelength of laser energy 20 that passes substantially through the outer tubular member 14 without being substantially absorbed thereby, but that will be substantially absorbed by the inner member 12.

When laser energy 20 is directed to the assembly 18, the energy 20 passes through the outer tubular member 14 without being significantly absorbed by the outer tubular member 14. When the energy 20 contacts the inner tubular member 12, at least some of the energy 20 is absorbed by the inner tubular member 12 which results in the affected portion of the inner tubular member 12 being heated.

Figure 2:
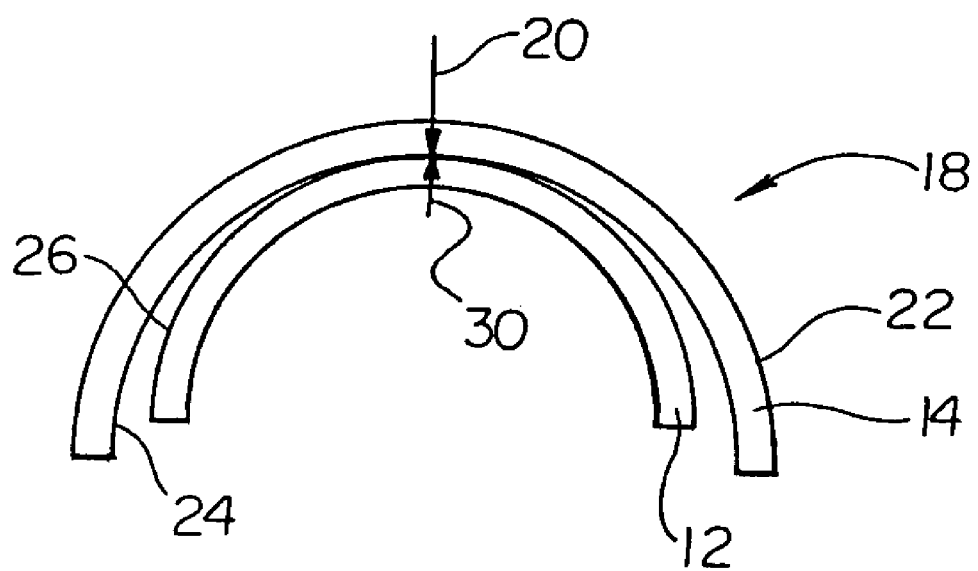
FIG. 2 is a close-up, cross sectional view of a tubular assembly shown in FIG. 1 shown prior to tack formation.

As is shown in FIG. 2, the heat, represented by arrow 30, produced by the absorption of energy 20 is sufficient to melt at least a portion of the outer surface 26 of the inner tubular member 12. The heat 30 is conductively transmitted to the inner surface 24 of the outer tube 14. In some embodiments the heat 30 is sufficient to melt at least a portion of the inner surface 24.

Figure 3:
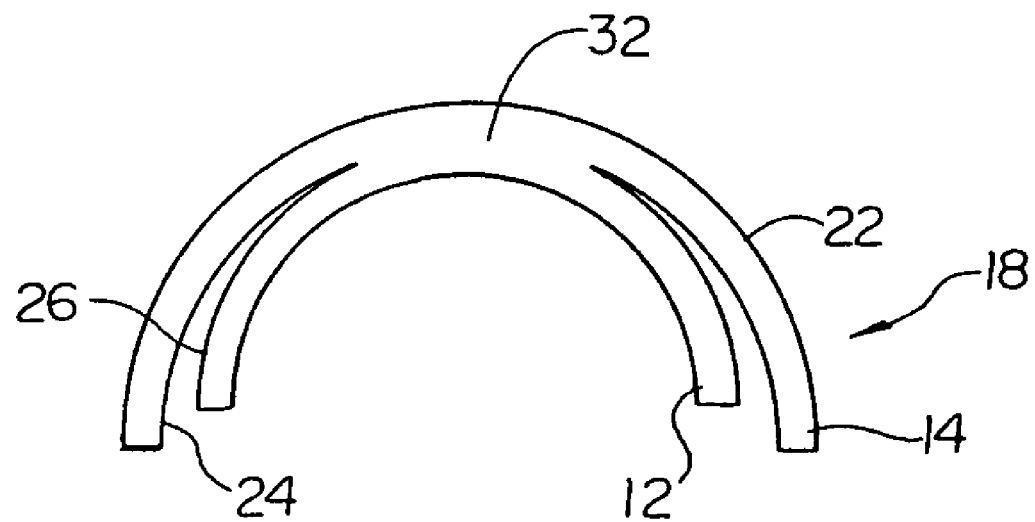
FIG. 3 is a close-up, cross sectional view of the tubular assembly shown in FIG. 2 shown during tack formation.

As is shown in FIG. 3, when laser energy 20 is removed from the assembly 18, the affected areas of the tubular members 12 and 14 are allowed to cool thereby forming a tack region 32 wherein at least the inner surface 24 of the outer tube 14 is engaged to at least the outer surface 26 of the inner member 12.

By allowing the inner tubular member 12 to be heated sufficiently to melt only a portion of the inner surface 24 of the outer tubular member 14 the tubular members may be tacked together without damaging the outer surface 22 of the outer member 12.

In some embodiments such as where the inner tubular member 12 is at least a portion of the inner tube of a catheter and the outer tubular member 14 is at least a portion of the outer tube of a catheter, the inner may be tacked or welded to the outer at a single point in the manner described. In some embodiments wherein the catheter comprises a balloon the inner may be tacked to the outer at a single point proximal to the balloon.

Before laser energy 20 can be applied to the catheter assembly 18, the tubular members 12 and 14 must be positioned so that the area of the inner member 12 and the area of the outer member 14 that correspond to the desired tack region 32 are immediately adjacent to one another.

In some embodiments of the invention, in order to position the tubular members 12 and 14 into a position suitable for forming tack region 32, a support mandrel or other elongate member 40 is positioned within inner lumen 13 as is shown in FIG. 1. The mandrel 40 may be fixedly or moveably positioned relative to a placement tray 42. Tray 42 defines a receipt region 49 which removably engages a first portion 44 of the outer tubular member 14 during tack formation.

An optical member 45, which acts as a window or lens through which laser energy 20 is passed prior to reaching assembly 18, is positioned opposite the placement tray 42 where it engages a second portion 48 of the outer tubular member 14.

Member 45 may be constructed of plastic, glass or other material that may be made suitable to act as a window or lens that is substantially transparent to the laser energy 20, or that may be suitable to define such a window or lens area 46.

Member 45 and tray 42 define a processing area 90 where assembly 18 is positioned for tacking. In order to properly tack the members 12 and 14 together the desired areas for formation of the tack must be held together under pressure. In some embodiments, positioning of the tubular members 12 and 14 is accomplished by providing apparatus 10 with a member 45 that is moveable relative to the tray 42.

By moving member 45 toward the tray 42, member 45 will apply a force toward an assembly 18 present in the processing area 90. During the tack formation process, member 45 will apply a "downward" pressure, indicated by arrow 47, to the outer tubular member 14, thereby pushing the desired area of the inner surface 24 of the outer tubular member 14 downward toward the outer surface 26 of the inner shaft 12.

In some embodiments mandrel 40 is moveable and may be used to push the inner tubular member 12 against the outer tubular member 14, as indicated by arrow 43. In some embodiments, both the mandrel 40 and the member 45 are moveable relative to one another.

Movement of member 45 and/or mandrel 40 is sufficient to place the inner surface 24 of the outer tubular member 14 into contact with the outer surface 26 of the inner shaft 12. Once the tubular members 12 and 14 are positioned as desired, laser energy 20 may be applied to the assembly 18.

In order to ensure that the outer surface 22 of the outer tubular member 14 is not damaged by the contact with the member 45, the bottom surface of the window 46 is provided with a substantially concave surface 41 which is shaped to have substantially the same radius of curvature as the outer tubular member 14. In some embodiments the radius of curvature of concave surface 41 is larger than that of the outer tubular member 14.

As a result, when the window 46 engages the second portion 48 of the outer shaft 14, any force applied to the outer shaft 14 by the window 46 or any force applied against the window 46 by the outer shaft 14 is uniformly distributed. Such uniform distribution of force allows the outer shaft 14 to be pressed into contact with the inner shaft 12 with minimal chance of abrading, puncturing, deforming or otherwise detrimentally affecting the outer shaft 14.

In some embodiments, the placement tray 42 may also employ a concave portion 49 that is shaped have substantially the same radius of curvature as the outer tubular member 14. However, as force is directed between the mandrel 40 and window 46, the tray 42 may employ other shapes as well without damaging the outer shaft 14.

In some embodiments the use of a mandrel is avoided. In such an embodiment the member 45 and tray 42 act to compress the outer member 14 therebetween. Compression of the outer member 14 will result in the outer surface 26 of the inner tubular member 12 contacting the inner surface 24 of the outer tubular member 14. In such an embodiment the inner tubular member 12 and outer tubular member 14 would also be in contact at one or more points adjacent to the receipt region 49 of the tray 42. In at least one embodiment the concave shape of the tray 42 will provide at least two contact points between the outer surface 26 of the inner tubular member 12 and the inner surface 24 of the outer tubular member 14, which are about 30 degrees apart depending on the curvature of the tray 42.

At least the portion of window 46 through which laser energy 20 is passed is substantially transparent to the energy 20. In order to ensure that energy 20 is passed only through a desired portion of the window 46, some embodiments of the invention include a mask 50. Mask 50 is positioned adjacent to the member 45 and defines an opening 52 through which the laser energy 20 is directed. The material of the mask 50 prevents laser energy 20 from passing through the mask material.

The opening 52 in the mask 50 may be any of a variety of cross-sectional shapes to provide a tack region 32 of a corresponding shape. For example, a substantially circular shaped opening 52 will allow a column of laser energy 20 having a substantially circular cross-section to be passed to the assembly 18 to form a tack region 32 having a size and shape substantially the same as to that of the opening 52.

In at least one embodiment of the invention opening 52 defines a substantially rectangular shape or other shape as desired.

Figure 4:
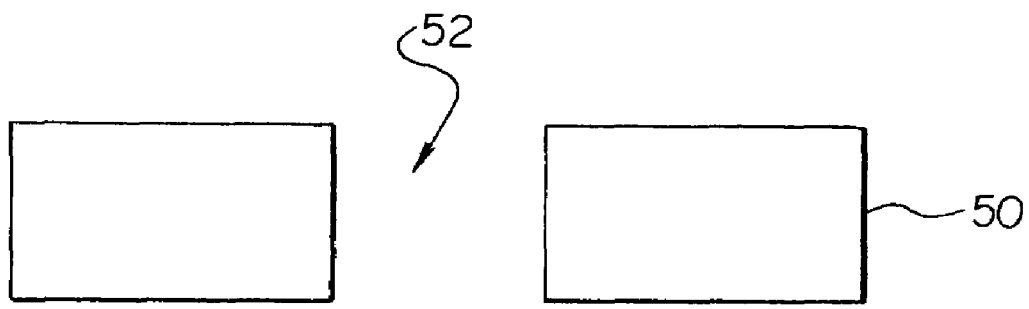
FIG. 4 is a cross-sectional view of an embodiment of a mask.

In some embodiments, such as in the example shown in FIG. 4, the opening 52 may have a cross-sectional shape having a substantially continuous size through the thickness of the mask 50. Alternatively, as is shown in FIG. 1 the opening 52 may be defined by a mask wall 54 that is tapered from a first diameter or width 56 at the top 58 of the mask 50 to a second narrower diameter or width 60 at the bottom 62 of the mask 50. In some cases the walls 54 of the mask 50 define an angle 64 relative to the window 46 of between about 10 degrees to about 20 degrees. In at least one embodiment angle 54 is about 15 degrees.

The size of the opening 52 at the bottom 62 of the mask 50 corresponds to the size of the tack region 32. The size of the tack region 32 may range from about 0.002 inches to about 0.02 inches. In some embodiments the size of the opening 52 and/or the tack region 32 is about 0.005 inches to about 0.015 inches. In at least one embodiment the size of the opening 52 and/or the tack region 32 is about 0.008 inches to about 0.012 inches.

The apparatus 10 provides for a method of forming extremely small tack regions relative to the size of weld or bond regions that many prior methods are capable of producing. By producing such small tack regions 32 a catheter assembly will have far less build up of webbing or other excess material that would otherwise potentially interfere with the performance characteristics of the catheter such as inflation and deflation times, an flexibility of the catheter.

Figure 5:
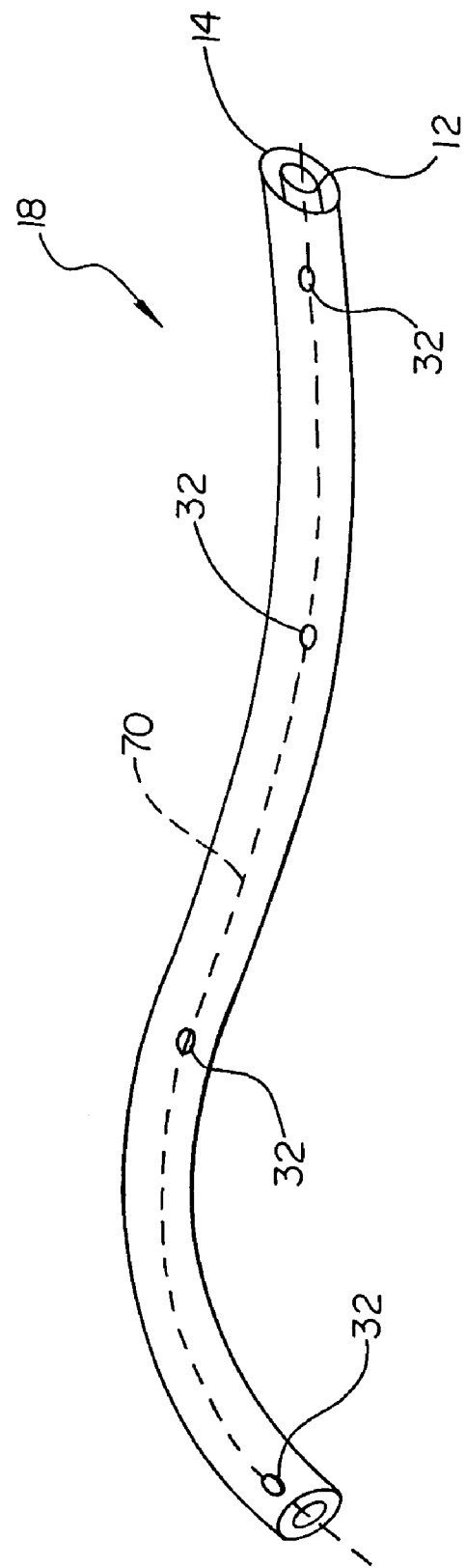
FIG. 5 is a perspective view of an embodiment of the invention.

Multiple tack regions 32 may be formed along a common longitudinal line 70 of the assembly 18 where the length of the tubular members 12 and 14 overlap, such as is shown in FIG. 5. However, it may be more desirable to distribute multiple tack regions 32 a predetermined number of degrees apart along the common length. For example, in FIG. 6 four tack regions 32 are distributed about 90 degrees apart from one another along a given length of the assembly 10, thereby providing the assembly 10 with a symmetrical radial distribution of the tack regions 32.

Figure 6:
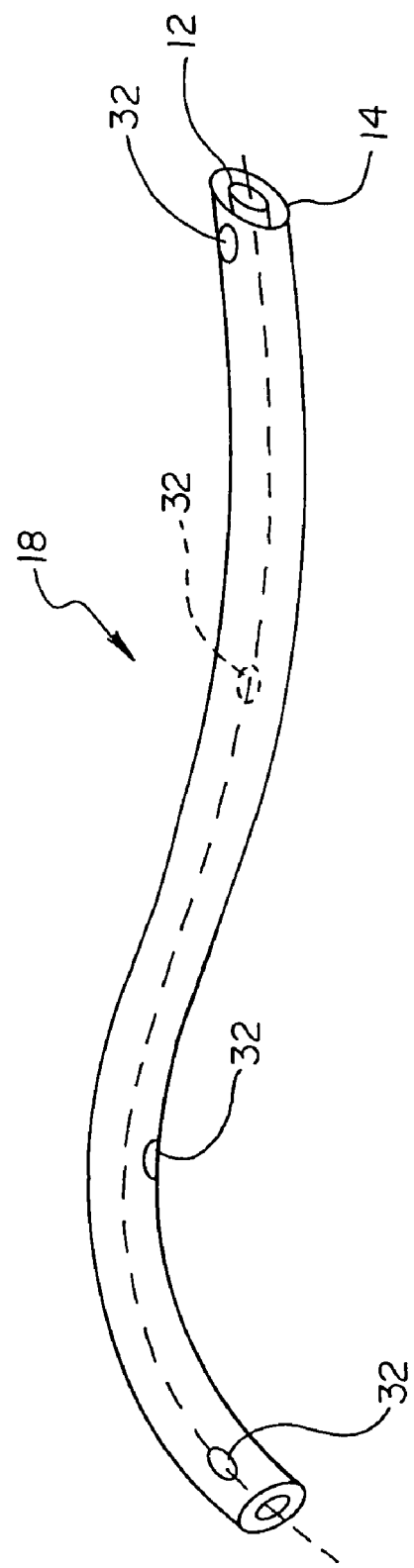
FIG. 6 is a perspective view of an embodiment of the invention.

Because symmetry of the tack regions 32 about the assembly 10 may be beneficial to the assembly's performance, the angular distribution of the tack regions 32 may be dependent on the number of tack regions. In FIG. 6, four regions 32 are distributed about 90 degrees apart, in an embodiment having three tack regions 32 the regions may be arranged about 120 degrees apart, five tack regions 32 may be distributed about 72 degrees apart, six tack regions may be distributed about 60 degrees apart, etc.

An additional benefit to providing a catheter assembly with one or more tack regions 32 is that the push response of the catheter assembly 18 may be improved by about 10 to about 30 percent. Due to the small size of the tack regions 32 the flexibility of the catheter assembly 18 is also improved. The use of apparatus 10 also avoids the use of a C-mandrel thus reducing the cost of processing the assembly 18.

In all of the various embodiments shown herein, the assembly 18, may be characterized as a catheter of any type.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. An apparatus for tacking materials together comprising:
   a laser, the laser constructed and arranged to selectively emit laser energy;
   an optical member, at least a portion of the optical member defining a window, the window being substantially transparent to the laser energy, the window having a first surface and a second surface, at least a portion of the second surface defining a substantially concave shape having a predetermined radius of curvature;
   a placement tray, the placement tray and the at least a portion of the second surface of the window define a processing area, at least a portion of the placement tray and the at least a portion of the second surface of the window being constructed and arranged to removably engage a tubular assembly within the processing area, the tubular assembly being defined by an outer tubular member disposed about at least a portion of at least one inner tubular member, the processing area constructed and arranged to receive the laser energy that is emitted from the laser and passed through the window of the optical member, the laser energy being transmitted substantially through the outer tubular member and being substantially absorbed by at least one region of the least one inner tubular member; and
   a moveable mandrel, the mandrel being positioned within the processing area, the mandrel constructed and arranged to be positioned at least partially within the at least one inner member of the tubular assembly.

2. The apparatus of claim 1 further comprising a mask, the mask constructed and arranged to prevent laser energy from passing therethrough, the mask being positioned immediately adjacent to the first surface of the optical member, the mask defining an aperture over the window of the optical member through which the laser energy is passed when emitted from the laser.

3. The apparatus of claim 2 wherein the aperture is substantially circular in shape.

4. The apparatus of claim 2 wherein the aperture is substantially rectangular in shape.

5. The apparatus of claim 2 wherein the mask has a thickness, the aperture having a substantially consistent diameter throughout the thickness of the mask.

6. The apparatus of claim 2 wherein the mask has a thickness, the aperture having a diameter which narrows from a first opening of a first diameter to a second opening of a second diameter through the thickness of the mask, wherein the second diameter is smaller than the first diameter.

7. The apparatus of claim 6 wherein the aperture is further defined by an aperture wall, the aperture wall forming an angle with the first surface of the optical member of about 10 to about 20 degrees.

8. The apparatus of claim 7 wherein the angle is about 15 degrees.

9. The apparatus of claim 2 wherein the aperture is about 0.002 inches to about 0.02 inches in diameter.

10. The apparatus of claim 2 wherein the aperture is about 0.005 inches to about 0.015 inches in diameter.

11. The apparatus of claim 2 wherein the aperture is about 0.008 inches to about 0.012 inches in diameter.

12. The apparatus of claim 6 wherein the second diameter is about 0.002 inches to about 0.02 inches.

13. The apparatus of claim 1 wherein the mandrel is constructed and arranged to push the at least one inner tubular member against the outer tubular member of the tubular assembly.

14. The apparatus of claim 1 wherein the optical member is moveable.

15. The apparatus of claim 14 wherein the optical member is constructed and arranged to push the outer tubular member against the at least one inner tubular member.

16. The apparatus of claim 1 wherein the optical member is moveable, the optical member constructed and arranged to push the outer tubular member against the at least one inner tubular member.

17. The apparatus of claim 1 wherein when the laser energy is substantially absorbed by the at least one region of the at least one inner tubular member a predetermined amount of heat is produced, the predetermined amount of heat causing the at least one region of the at least one inner tubular member to at least partially melt.

18. The apparatus of claim 17 wherein the outer tubular member defines an inner surface and an outer surface, at least a portion of the inner surface being immediately adjacent to the at least one region of the at least one inner tubular member, at least a portion of the predetermined amount of heat is conductively transferred from the at least one region of the at least one inner tubular member to the at least a portion of the inner surface of the outer tubular member.

19. The apparatus of claim 18 wherein the at least a portion of the predetermined amount of heat causes the at least a portion of the inner surface of the outer tubular member to melt.

20. The apparatus of claim 19 wherein subsequent to melting the at least a portion of the inner surface of the outer tubular member, the laser stops emitting the laser energy and the predetermined amount of heat dissipates from the tubular assembly to cool the at least one region of the at least one inner tubular member and the at least a portion of the inner surface of the outer tubular member together to define at least one tack region.

21. The apparatus of claim 19 wherein the at least one tack region is substantially circular in shape.

22. The apparatus of claim 19 wherein the at least one tack region is substantially rectangular in shape.

23. The apparatus of claim 19 wherein the at least one tack region is about 0.002 inches to about 0.02 inches in diameter.

24. The apparatus of claim 19 wherein the at least one tack region is about 0.005 inches to about 0.015 inches in diameter.

25. The apparatus of claim 19 wherein the at least one tack region is about 0.008 inches to about 0.012 inches in diameter.

26. The apparatus of claim 19 wherein the tubular assembly defines a predetermined length, the at least one tack region comprises a plurality of tack regions positioned along the predetermined length of the tubular assembly.

27. The apparatus of claim 26 wherein the plurality of tack regions are positioned along the predetermined length of the tubular assembly along a common longitudinal line.

28. The apparatus of claim 26 wherein the plurality of tack regions are positioned apart from one another about a circumference of the inner tubular member, each of the tack regions being separated by a predetermined angle, the predetermined angle between each tack region being substantially the same.

29. The apparatus of claim 28 wherein the plurality of tack regions are positioned substantially equidistant from each other relative to a longitudinal axis of the tubular assembly.

* * * * *